United States Patent
Williams et al.

(10) Patent No.: US 12,295,603 B2
(45) Date of Patent: May 13, 2025

(54) METHOD OF SECURING THE SHAFT OF A SURGICAL INSTRUMENT TO THE INSTRUMENT HOUSING

(71) Applicant: Conmed Corporation, Largo, FL (US)

(72) Inventors: Mason Williams, Centennial, CO (US); Julia Concelman, Cranberry Township, PA (US)

(73) Assignee: Conmed Corporation, Largo, FL (US)

(*) Notice: Subject to any disclaimer, the term of this patent is extended or adjusted under 35 U.S.C. 154(b) by 857 days.

(21) Appl. No.: 17/293,629

(22) PCT Filed: Nov. 13, 2019

(86) PCT No.: PCT/US2019/061075
§ 371 (c)(1),
(2) Date: May 13, 2021

(87) PCT Pub. No.: WO2020/102275
PCT Pub. Date: May 22, 2020

(65) Prior Publication Data
US 2022/0015788 A1 Jan. 20, 2022

Related U.S. Application Data

(60) Provisional application No. 62/767,014, filed on Nov. 14, 2018.

(51) Int. Cl.
*A61B 17/29* (2006.01)
*A61B 17/00* (2006.01)

(52) U.S. Cl.
CPC .... *A61B 17/29* (2013.01); *A61B 2017/00367* (2013.01); *A61B 2017/2902* (2013.01); *A61B 2017/2929* (2013.01)

(58) Field of Classification Search
CPC .......... A61B 17/29; A61B 2017/00367; A61B 2017/2902; A61B 2017/2929
See application file for complete search history.

(56) References Cited

U.S. PATENT DOCUMENTS

2005/0216022 A1* 9/2005 Lechot ............... A61B 17/1666
606/81
2012/0296333 A1* 11/2012 Twomey ............ A61B 17/2909
606/52

(Continued)

FOREIGN PATENT DOCUMENTS

DE 10156917 6/2003
EP 3241510 11/2017

(Continued)

OTHER PUBLICATIONS

Wikipedia Article on "Circlips" dated Dec. 2016, retrieved from Internet Archive as of Jan. 24, 2024, PDF attached (Year: 2016).*

(Continued)

Primary Examiner — Lynsey C Eiseman
Assistant Examiner — Amanda L Steinberg
(74) Attorney, Agent, or Firm — Bond, Schoeneck & King, PLLC; David L. Nocilly (57) ABSTRACT

A surgical instrument having a housing, an outer shaft extending from the housing along a longitudinal axis, an inner shaft extending within the outer shaft along the longitudinal axis, a rotator knob position about the outer shaft, and a tube stop coupling the rotator knob to the outer shaft for collective rotation about the longitudinal axis and fixed within the housing against movement along the longitudinal axis. The tube stop has a pair of bearing surfaces that extend into a pair of longitudinal tracks of the outer shaft, and the rotator knob includes a pair of rails that extend into the pair of tracks of the outer shaft and block the tube stop exiting the tracks. The tube stop is captured between a pair of ribs in the (Continued)

housing to hold the tube stop in place while allowing the rotator knob to rotate the outer shaft.

6 Claims, 9 Drawing Sheets

(56) References Cited

U.S. PATENT DOCUMENTS

2017/0319229 A1* 11/2017 Brown ........... A61B 17/320068
2021/0030436 A1* 2/2021 Swearingen ... A61B 17/320092

FOREIGN PATENT DOCUMENTS

| JP | 1992-246344 | A2 | 9/1992 |
| JP | 2017-200582 | A2 | 11/2017 |
| WO | 2017/100412 | | 6/2017 |

OTHER PUBLICATIONS

JP Office Action, App. No. 2021-525716, dated Jul. 12, 2022, pp. 1-9.
International Search Report Form PCT/ISA/220, International Application No. PCT/US2019/061075, pp. 1-10, Dated Feb. 13, 2020.

* cited by examiner

METHOD OF SECURING THE SHAFT OF A SURGICAL INSTRUMENT TO THE INSTRUMENT HOUSING

CROSS-REFERENCES TO RELATED APPLICATIONS

This application is a national stage application under 35 U.S.C. 371 based on international patent application PCT/US19/61075 filed on Nov. 13, 2019, which claims priority to U.S. Provisional Patent Application Ser. No. 62/767,014 filed on Nov. 14, 2018, the entireties of which are incorporated herein by reference.

BACKGROUND OF THE INVENTION

1. Field of the Invention

The present invention relates to surgical instruments and, more specifically, to an approach for securing an elongated shaft to a housing for rotational movement.

2. Description of the Related Art

Surgical instruments, such as vessel sealers and like, include a handle from which a shaft extends and supports a surgical implement, such as a pair of jaws, that may be operated by a surgeon to perform a procedure. Positioning of the implement with a patient may require rotation of the entire surgical instrument to rotate the implement at the end of the shaft. For example, in order to position the jaws of a vessel sealer about a vessel, the jaws may need to be rotated by the surgeon so that the jaws can encompass the vessel prior to closing the jaws. As a result, there is a need in the art for an approach that can allow a user to more easily rotate the implement at the end of the shaft during a procedure so that the instrument can be more properly aligned for the procedure.

BRIEF SUMMARY OF THE INVENTION

The present invention secures the shaft of a surgical instrument to the housing of the instrument while allowing for rotation of the shaft via a rotator knob. More specifically, the present invention comprises a surgical instrument having a housing, an outer shaft extending from the housing along a longitudinal axis, an inner shaft extending within the outer shaft along the longitudinal axis, a rotator knob position about the outer shaft, and a tube stop coupling the rotator knob to the outer shaft for collective rotation about the longitudinal axis and fixed within the housing against movement along the longitudinal axis. A pair of tracks extend longitudinally in the outer shaft. The tube stop has a pair of bearing surfaces that extend into the pair of tracks, respectively. The rotator knob includes a pair of rails that extend into the pair of tracks of the outer shaft, respectively. Each of the pair of tracks include a first portion extending longitudinally in the outer shaft and a second portion extending circumferentially from an end of the first portion. Each of the pair of bearing surfaces of the tube stop are positioned in the second portion of each of the pair of tracks, respectively. The rails of the rotator knob extend to the end of the portion of each of the tracks to block the tube stop from rotation out of the second portion of each of the tracks. The tube stop is captured between a pair of ribs in the housing. The tube stop includes a second pair of bearing surfaces that engage the outer shaft. The tube stop includes a third pair of bearing surfaces that engage the ribs of the rotator knob.

The present invention also includes a method of coupling elements of a surgical instrument for common rotation. The method includes the steps of providing a housing, an outer shaft extending from the housing along a longitudinal axis, an inner shaft extending within the outer shaft along the longitudinal axis, positioning a tube stop about the outer shaft, positioning a rotator knob about the outer shaft in abutment with the tube stop and in interlocking engagement with the outer shaft, and fixing the tube stop within the housing to prevent movement of the tube stop along the longitudinal axis. The rotator knob includes a pair of rails that extend within a pair of tracks of the outer shaft, respectively. A pair of bearing surfaces of the tube stop extend into the pair of tracks, respectively, and are fixed in place by the pair of rails of the rotator knob. Each of the pair of tracks includes a first portion that accepts one of the pair of rails of the rotator knobs and a second portion that extends circumferentially from the first portion and accepts one of the bearing surfaces of the tube stop.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
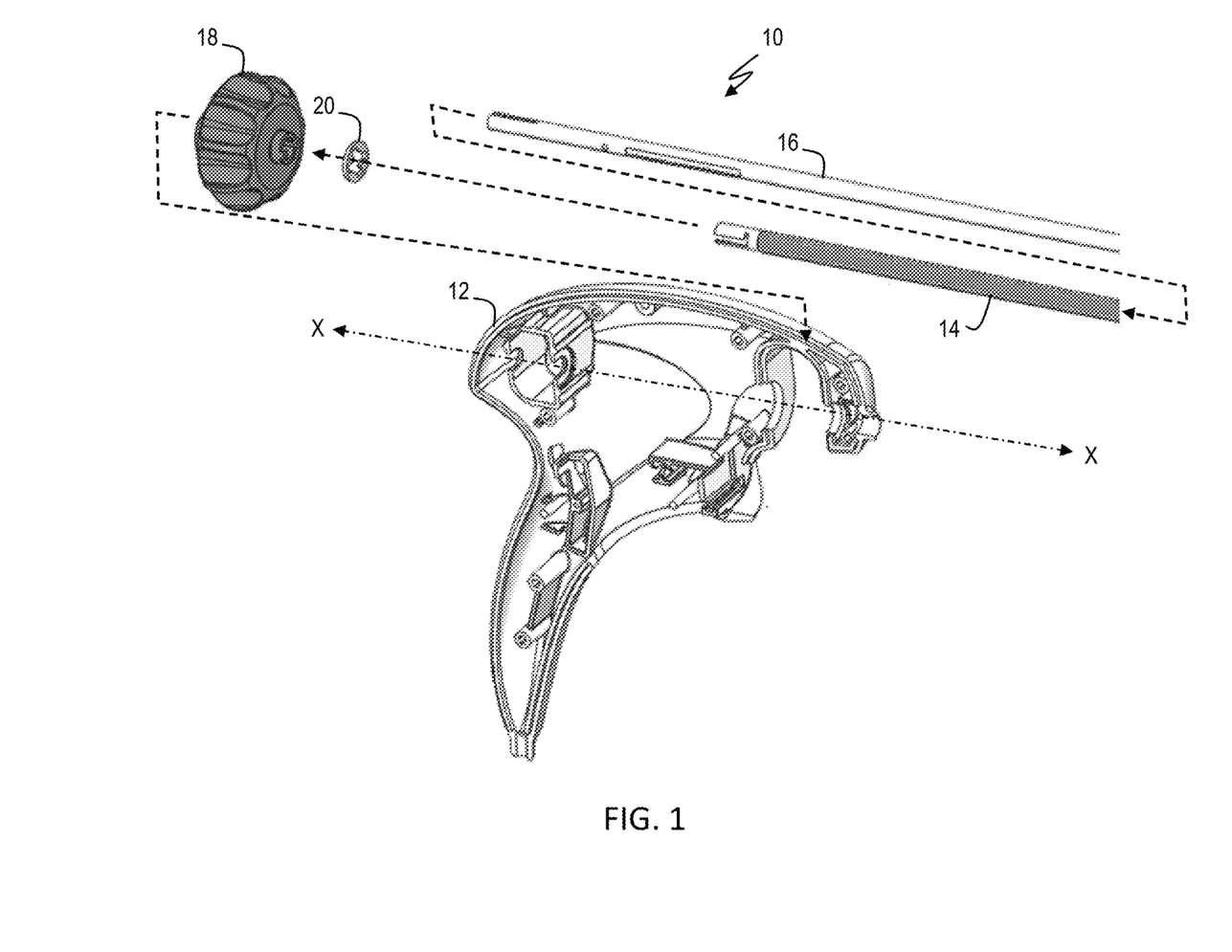
FIG. 1 is an exploded isometric view of a surgical instrument according to the present invention.

Referring to the figures, wherein like numeral refer to like parts throughout, there is seen in FIG. 1 a surgical instrument 10 having a housing 12. As in known in the art, housing 12 is shaped to allow a surgeon to grasp a proximal end of surgical instrument 10 for use during a surgical procedure. Surgical instrument 10 further comprises an outer shaft 14 that extends distally from a portion of housing 12 along a longitudinal axis X-X. An inner shaft 16 that extends within outer shaft 14. A rotator knob 18 is interconnected to outer shaft 14 to allow a user to rotate outer shaft 14. A tube stop 20 engages both outer shaft 14 and rotator knob 18 to interlock outer shaft 14 and rotator knob 18 for common rotation.

Figure 2:
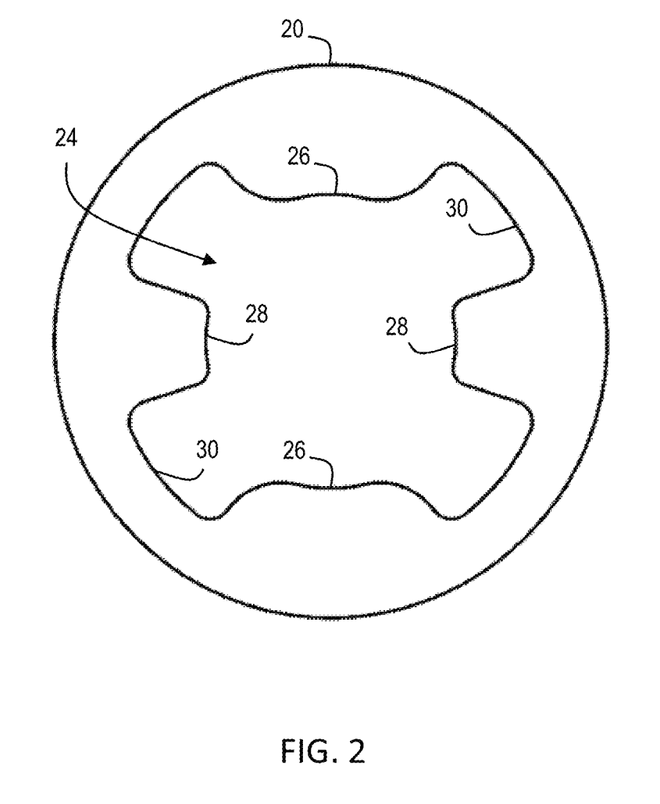
FIG. 2 is an end view of a tube stop according to the present invention.
Figure 7A:
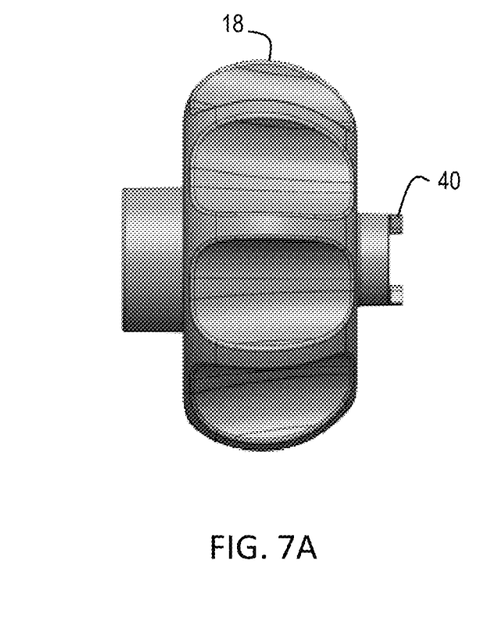
FIG. 7A is a side view a rotator knob according to the present invention.
Figure 7B:
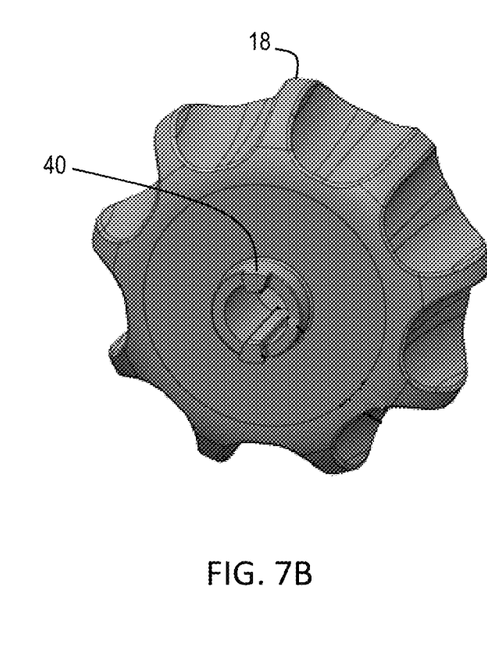
FIG. 7B is a perspective view of a rotator knob according to the present invention.

Referring to FIG. 2, tube stop 20 comprises a body 22 formed as a disk and including an opening 24 therethrough. Opening 24 is defined by a first set of bearing surfaces 26, a second set of bearing surfaces 28, and a third set of bearing surfaces 30. First set of bearing surfaces 26 engage the outer surface 32 of outer shaft 14. Second set of bearing surfaces 28 engage the outer surface 34 of inner shaft 16 via a corresponding pair of tracks 36 formed through outer shaft 14. Third set of surfaces 30 engage a pair of corresponding rails 40 extending longitudinally from rotator knob 18, as seen in FIGS. 7A and 7B.

Figure 3:
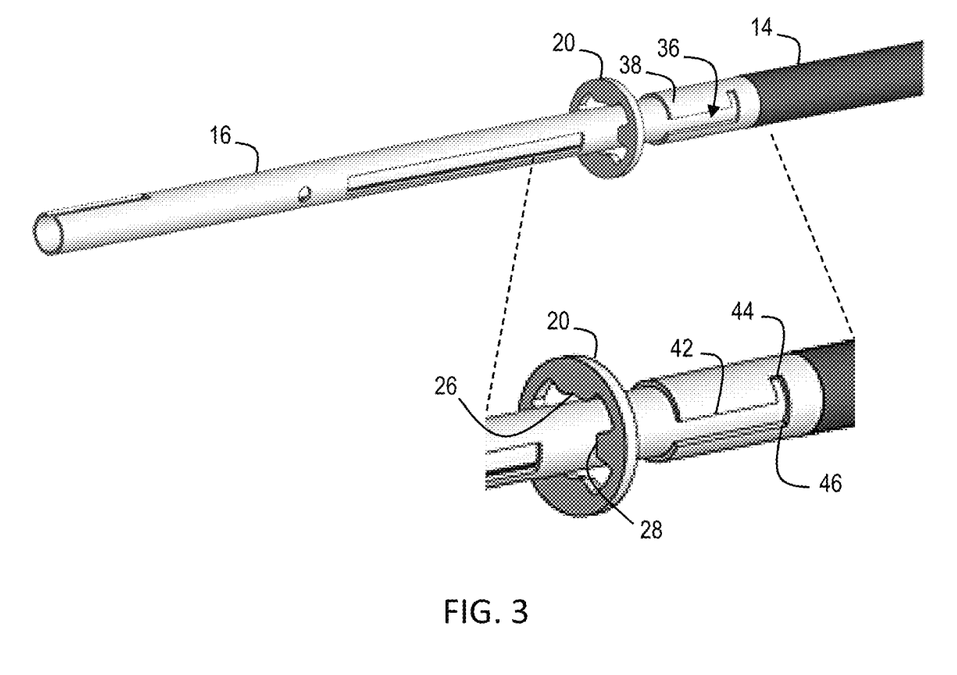
FIG. 3 is a perspective view of the positioning of a tube stop over the inner and outer shafts of a surgical instrument according to the present invention.
Figure 4:
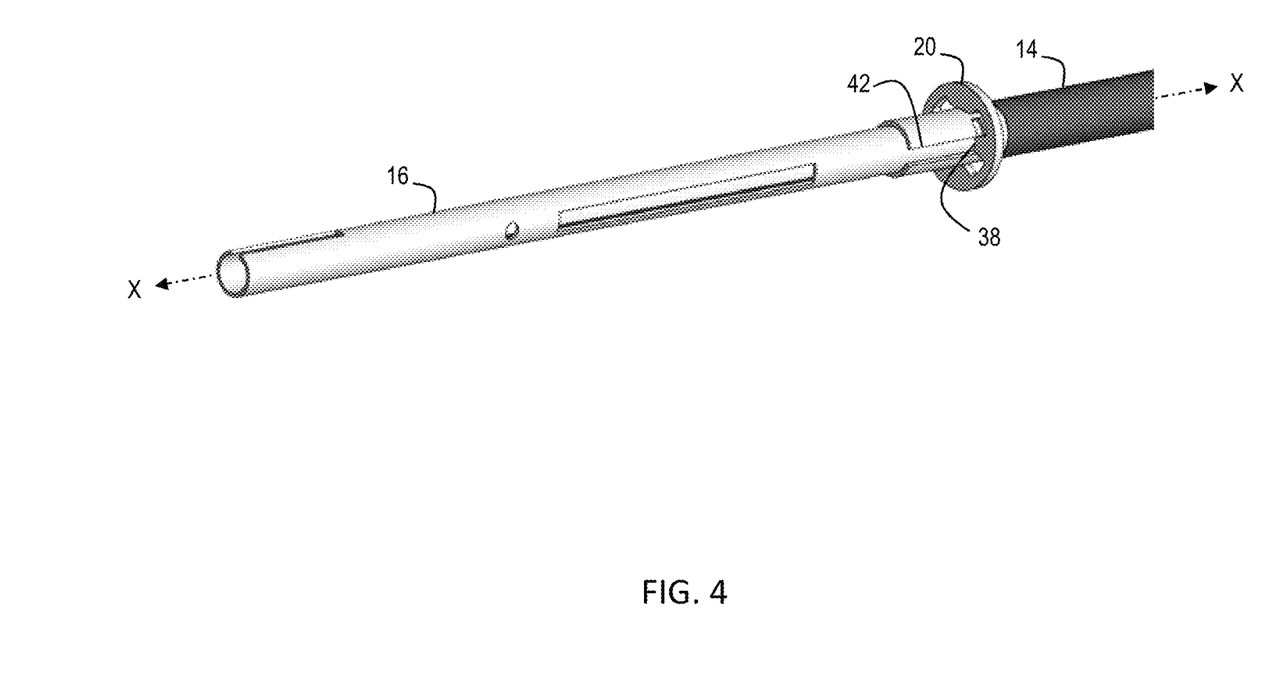
FIG. 4 is a perspective view of the positioning of a tube stop over the inner and outer shafts of a surgical instrument according to the present invention.
Figure 5:
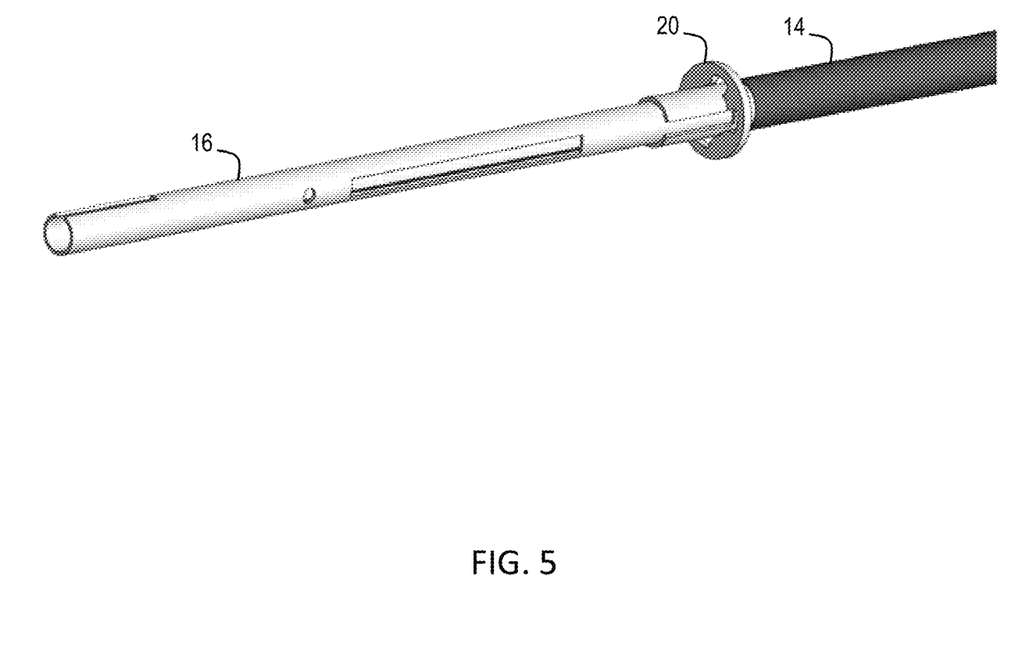
FIG. 5 is a perspective view of the positioning of a tube stop over the inner and outer shafts of a surgical instrument according to the present invention.

Referring to FIG. 3, tube stop 20 is positioned about outer shaft 14 and inner shaft 16 is positioned within outer shaft 14. Second set of bearing surfaces 28 are aligned with tracks 36 formed into the outer surface 38 of outer shaft 14. As seen in FIG. 4, tracks 36 include a first portion 42 that extends longitudinally in parallel with axis X-X from the end of outer shaft 14 from the end of outer shaft 14 to an internal end 46. A second portion 44 extends circumferentially about a portion of outer shaft 14 from end 46 of first portion 42 at right angles to first portion 42 and thus axis X-X. As seen in FIG. 5, second portion 44 is in communication with first portion 42 so that second set of bearing surfaces 28 of tube stop 20 may be passed along first portion 42 and then rotated into second portion 44, thereby capturing second set of bearing surfaces 28 within second portion 44 of tracks 36 and preventing longitudinal movement of bearing surfaces 28.

Figure 6:
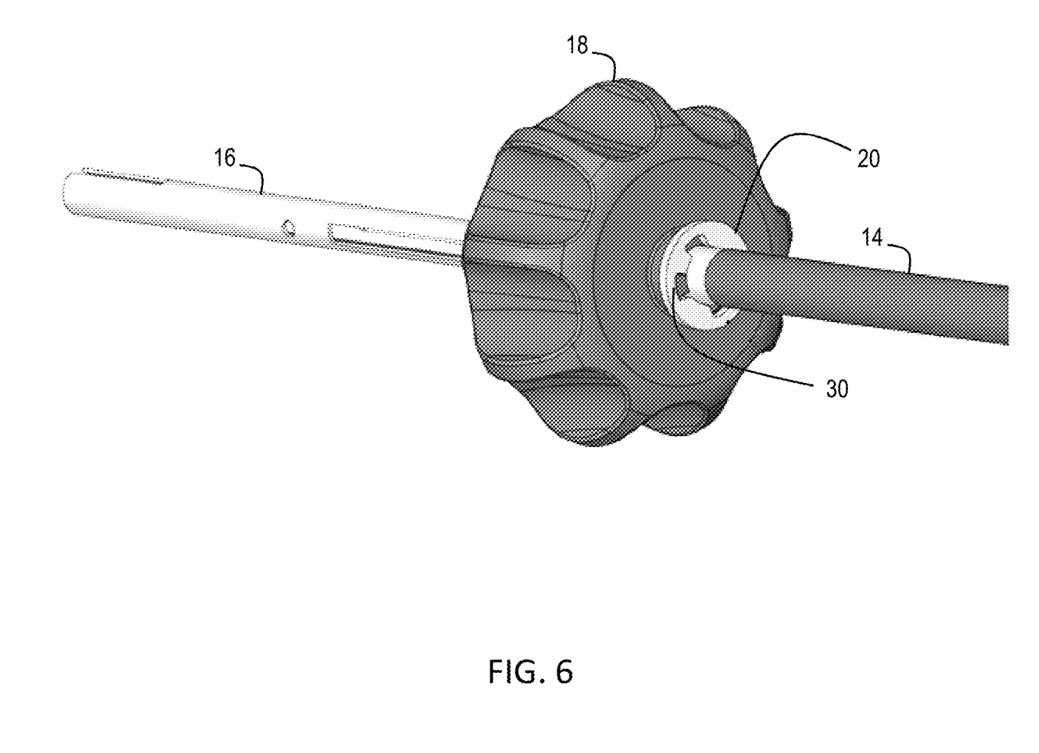
FIG. 6 is a perspective view of the positioning of a rotator knob over the inner and outer shafts of a surgical instrument according to the present invention.

Referring to FIG. 6, rotator knob 18 is passed over inner shaft 16 so that rails 40 engage third set of bearing surfaces 30. Rails 40 are shaped to slide along tracks 36 of outer shaft 14 to end 46 of first portion 42, thereby blocking tube stop 20 from rotating out of second portion 44 of tracks 36. The interconnection between rails 40 of rotator knob 18 and tracks 36 interlocks rotator knob 18 with outer shaft 14 for co-rotation therewith. Third set of bearing surfaces 30 capture rails 40 securely to hold rails within tracks 36.

Figure 8:
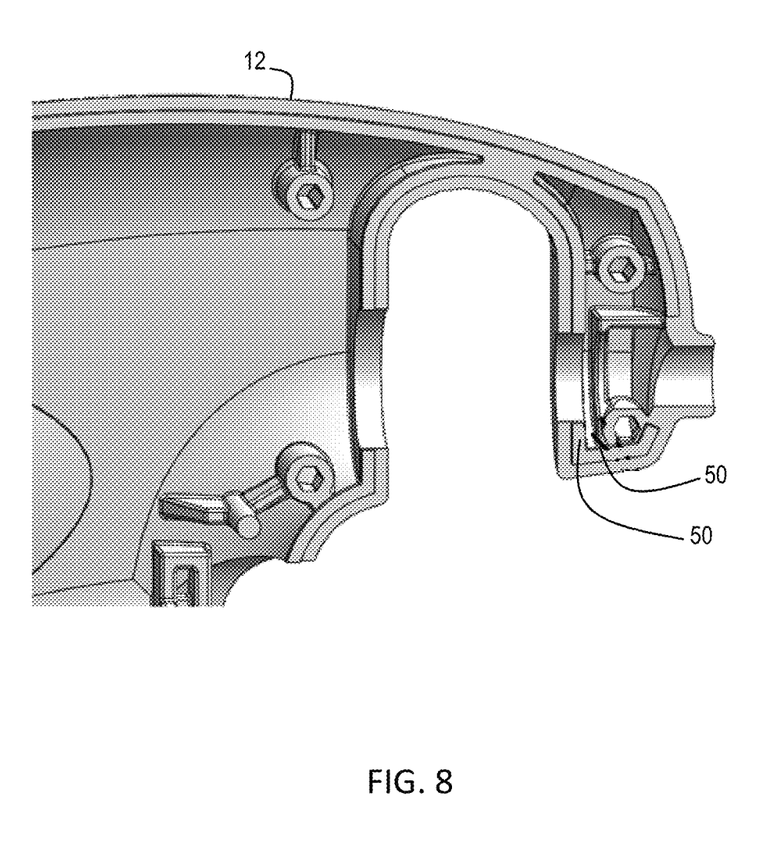
FIG. 8 is side view of the inner surface of a housing according to the present invention.
Figure 9:
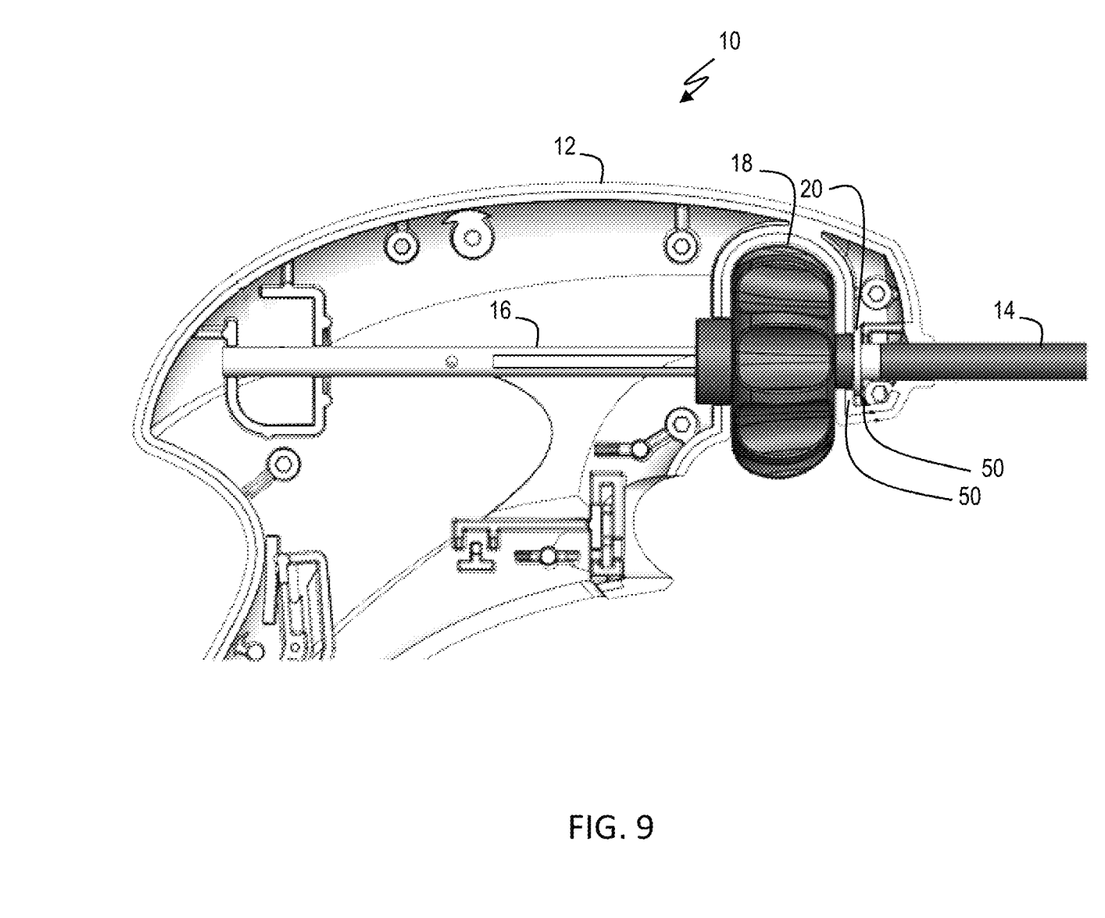
FIG. 9 is a side view of the inner surface of a housing with a rotator knob and tube stop in position according to the present invention.

Referring to FIG. 8, housing 12 includes a pair of spaced apart ribs 50 positioned to capture and hold tube stop 20 within housing 12. Ribs 50 thus prevent proximal or distal movement of tube stop 20 along axis X-X, thereby securing outer shaft 14 relative to housing 12, as seen in FIG. 9. Inner shaft 16 extends proximally through housing 12 and is capable of longitudinal movement along axis X-X while shaft 14 is fixed against movement. Rotation of rotator knob 18 will cause rotation of outer shaft 14 but not inner shaft 16. As is known in the art, inner shaft 16 may be coupled to a mechanism in housing 12 that can cause movement of inner shaft 16 relative to outer shaft 14 to drive a surgical implement positioned at the distal end of inner shaft 16, such as a pair of opposing jaws or the like.

What is claimed is:

1. A surgical instrument, comprising:
   a housing;
   an outer shaft extending from the housing along a longitudinal axis and having a pair of tracks extending longitudinally in an end of the outer shaft;
   an inner shaft extending within the outer shaft and along the longitudinal axis;
   a rotator knob positioned directly around and contacting the outer shaft adjacently to the end of the shaft, wherein the rotator knob includes a pair of rails that each have a first portion that extends inwardly from the rotator knob to directly engage the pair of tracks of the outer shaft and a second portion that extends longitudinally from the rotator knob; and
   a tube stop positioned directly around the end of the shaft in abutting relation to the rotator knob relative to the longitudinal axis and having a first pair of bearing surfaces extending directly into the pair of tracks, respectively, a second pair of bearing surfaces abutting the outer shaft, and a third pair of bearing surfaces engaging the second portion of the pair of rails that extends longitudinally from the rotator knob, wherein the tube stop blocks the rotator knob from longitudinal movement along the longitudinal axis.

2. The surgical instrument of claim 1, wherein each of the first pair of bearing surfaces of the tube stop are positioned in the second portion of each of the pair of tracks, respectively.

3. The surgical instrument of claim 2, wherein the pair of rails of the rotator knob extend to an end of the portion of each of the tracks to block the tube stop from rotation out of the second portion of each of the tracks.

4. The surgical instrument of claim 3, where the tube stop is captured between a pair of ribs in the housing.

5. A method of coupling elements of a surgical instrument for common rotation, comprising the steps of:
   providing a housing, an outer shaft extending from the housing along a longitudinal axis and having a pair of tracks extending longitudinally in an end of the outer shaft, an inner shaft extending within the outer shaft and along the longitudinal axis;
   positioning a tube stop directly around the end of the shaft and in abutting relation to the rotator knob relative to the longitudinal axis, wherein the tube stop has a first pair of bearing surfaces extending into the pair of tracks, respectively, a second pair of bearing surfaces abutting the outer shaft, and a third pair of bearing surfaces;
   positioning a rotator knob including a pair of rails having a first portion that extends inwardly from the rotator knob and a second portion that extends longitudinally from the rotator knob about the outer shaft so that the first portion of the pair of rails extends into the pair of tracks of the outer shaft, respectively, and the second portion of the pair of rails engages the third pair of bearing surfaces of the tube stop, wherein the rotator knob is in abutment with the tube stop along the longitudinal axis and in interlocking engagement with the outer shaft; and
   fixing the tube stop within the housing to prevent movement of the tube stop and the rotator knob along the longitudinal axis.

6. The method of claim 5, wherein each of the pair of tracks includes a first portion that accepts one of the pair of rails of the rotator knobs and a second portion that extends circumferentially from the first portion and accepts one of the bearing surfaces of the tube stop.

* * * * *